(12) United States Patent
Kohls et al.

(10) Patent No.: US 8,594,771 B2
(45) Date of Patent: Nov. 26, 2013

(54) DEVICES AND METHODS FOR SELF-ADMINISTERED ECG EXAMINATIONS

(75) Inventors: Mark Robert Kohls, New Berlin, WI (US); Sarah Beth Alme, Milwaukee, WI (US); Richard Andrew Valiga, Waukesha, WI (US); John Edward Lorbiecki, Hubertus, WI (US); Joel Qiuzhen Xue, Germantown, WI (US); Brian Joseph Young, Germantown, WI (US); James Russel Peterson, Fond du Lac, WI (US); Lawrence Elwood Murphy, Shorewood, WI (US)

(73) Assignee: General Electric Company, Schenectady, NY (US)

(*) Notice: Subject to any disclaimer, the term of this patent is extended or adjusted under 35 U.S.C. 154(b) by 740 days.

(21) Appl. No.: 11/610,995

(22) Filed: Dec. 14, 2006

(65) Prior Publication Data

US 2007/0149888 A1    Jun. 28, 2007

Related U.S. Application Data

(63) Continuation-in-part of application No. 11/319,640, filed on Dec. 28, 2005, now abandoned.

(51) Int. Cl.
*A61B 5/02*    (2006.01)
(52) U.S. Cl.
USPC .......................... 600/509; 600/508; 600/519
(58) Field of Classification Search
USPC ................... 600/508, 519, 323, 365
See application file for complete search history.

(56) References Cited

U.S. PATENT DOCUMENTS

| 41,804 A | 3/1864 | Woolworth |
| 4,531,527 A * | 7/1985 | Reinhold et al. ............... 600/509 |

(Continued)

FOREIGN PATENT DOCUMENTS

| CN | 1289340 A | 3/2001 |
| CN | 2659055 Y | 11/2004 |

(Continued)

OTHER PUBLICATIONS http://www.healthfrontier.com/Products/product_detail.cfm?productid=1.

(Continued)

*Primary Examiner* — Joseph Stoklosa
(74) *Attorney, Agent, or Firm* — Global Patent Operation; Marc A. Vivenzio

(57) ABSTRACT

Devices and methods comprise or provide an ECG recording device containing a mailable base and electrode assembly and/or other means engageable with the base to receive ECG signals from a subject during a self-administered ECG examination. The devices and methods may also include a single-use or limited-use ECG recording device, in which the base is disposable or reusable or recyclable. In addition, the device may be self-contained, battery-operated, portable, disposable, mailable to a location remote from an ECG examination, provide feedback, indicate its method of use, including graphically depicting same, contain a finger cuff and/or sensor pad for receiving ECG signals, and/or contain a memory. Preferably, the base conforms to various body shapes and/or sizes, is made of flexible and/or semi-flexible material, and/or contains a receptor, such as sealable blood well. The device can also communicate the ECG signals to an ECG processing system, which can be remote from the ECG examinations and comprise wireless communications.

33 Claims, 5 Drawing Sheets

(56) References Cited

U.S. PATENT DOCUMENTS

| | | | |
|---|---|---|---|
| 5,191,891 A * | 3/1993 | Righter | 600/523 |
| 5,713,365 A | 2/1998 | Castelli | |
| 6,075,150 A | 6/2000 | Wang et al. | |
| 6,244,462 B1 | 6/2001 | Ehrensvard et al. | |
| 6,301,502 B1 | 10/2001 | Owen et al. | |
| 6,363,274 B1 * | 3/2002 | Scalisi et al. | 600/523 |
| 6,558,320 B1 | 5/2003 | Causey, III et al. | |
| 6,580,943 B2 * | 6/2003 | Nissila | 600/509 |
| 6,701,183 B2 | 3/2004 | Baker et al. | |
| 6,730,025 B1 | 5/2004 | Platt | |
| 6,800,059 B2 | 10/2004 | Muraki et al. | |
| 7,236,818 B2 | 6/2007 | McLeod et al. | |
| 2002/0115912 A1 | 8/2002 | Muraki et al. | |
| 2003/0109772 A1 * | 6/2003 | Mills | 600/310 |
| 2003/0167075 A1 | 9/2003 | Fincke | |
| 2005/0010087 A1 * | 1/2005 | Banet et al. | 600/300 |
| 2007/0100213 A1 * | 5/2007 | Dossas et al. | 600/300 |

FOREIGN PATENT DOCUMENTS

| | | | |
|---|---|---|---|
| FR | 2519856 A | | 7/1983 |
| JP | 59044242 A | | 3/1984 |
| JP | 7-275217 A | | 10/1995 |
| JP | 09-117420 | | 5/1997 |
| JP | 2000-83907 A | | 3/2000 |
| JP | 2001149327 A | | 6/2001 |
| JP | 2001-245863 A | | 9/2001 |
| JP | 2002501775 A | | 1/2002 |
| JP | 2002-45343 A | | 2/2002 |
| JP | 2003-070759 A | | 3/2003 |
| JP | 2005000468 A | | 1/2005 |
| JP | 2006247075 A | | 9/2006 |
| WO | 9401040 A | | 1/1994 |
| WO | 2005018447 A1 | | 3/2005 |
| WO | 2006034291 A2 | | 3/2006 |

OTHER PUBLICATIONS http://www.winhealth.co.uk/ECG.htm.
http://www.dcbiomed.com/web/hanecg4.htm.
http://www.lifesynccorp.com.
"Ecg@home." HealthFrontier—web-based & wireless ECG/EKG cardiology. http://www.healthfrontier.com/Products/product_detail.cfm?productid=1, Dec. 14, 2006, p. 1-4.
Unofficial English translation of JP Office Action from corresponding JP Application No. 2007-311850, dated Jul. 10, 2012.
Search Report and Written Opinion from corresponding EP Application No. 06126333.1, dated Aug. 13, 2007.
Office Action from corresponding U.S. Appl. No. 11/319,640, dated Jun. 25, 2008.
Unofficial English translation of JP Office Action from corresponding JP Application No. 2006-349662, dated Mar. 27, 2012.
Unofficial Translation of JPO Notice of Allowance from corresponding JP Application 2007-311850 dated Jan. 22, 2013.

* cited by examiner

DEVICES AND METHODS FOR SELF-ADMINISTERED ECG EXAMINATIONS

CROSS-REFERENCE TO RELATED APPLICATION

This application is a continuation-in-part of U.S. patent application Ser. No. 11/319,640, which was filed on Dec. 28, 2005 and entitled "ECG Recording Device and Method of Use."

STATEMENT REGARDING FEDERALLY SPONSORED RESEARCH OR DEVELOPMENT

-

REFERENCE(S) TO MICROFICHE APPENDIX AND/OR COPYRIGHT PROTECTION

-

BACKGROUND

1. Field

In general, the inventive arrangements relate to diagnostic cardiology, and more specifically, to self-administering electrocardiogram ("ECG") examinations at locations remote from traditional points-of-care.

2. Description of Related Art

For illustrative, exemplary, representative, and non-limiting purposes, preferred embodiments of the inventive arrangements will be described in terms of cardiac monitoring. However, the inventive arrangements are not limited in this regard.

Now then, syncope (i.e., sudden loss of consciousness) and arrhythmias (i.e., abnormal rhythms) resulting from electrical instability within the heart are particularly challenging for cardiologists to observe. These events can be of short duration and sudden onset, and they often occur infrequently. Early diagnosis of arrhythmias is important, however, because there is a greater likelihood that a patient may suffer a heart failure, stroke, permanent damage, and/or death depending on how long a particular arrhythmia continues undetected and/or untreated. Several arrhythmia-related diseases, such as genetic Long QT Syndrome (LQTS), Wolff-Parkinson-White Syndrome, and Brugada Syndrome, for example, are genetic; others, such as drug-induced LQTS, can be acquired using certain pharmaceuticals.

One effective method for diagnosing arrhythmia-related problems and/or the like involves using electrocardiograms ("ECGs") for monitoring the electrical activity in a subject's heart. Typically, electric leads are placed on the subject's body at specific locations, and the electrical activity resulting from the heart's polarization and depolarization is then recorded by each lead. During a typical cardiac cycle, for example, the ECG produces a distinctive waveform, often comprising a P-wave, QRS complex, and T-wave, which can then be analyzed to diagnose and/or assess the efficacy of a treatment, such as, for example, a particular drug therapy.

Often, portable ECG recorders are used to collect ECG data from patients after an initial ECG is taken at a physician's office, clinic, and/or other healthcare facility, likely using a traditional, on-site, non-ambulatory ECG recorder. ECG recordings from these portable devices can be used to detect abnormalities in the electrical activity of a patient's heart, which can be caused, for example, by a patient's routine activities and/or heightened emotional and/or physical states.

Commonly, such portable ECG recorders are constructed of two types. The first type is a time-delayed system, which can analyze collected data after completing a collection phase. The second type is a real-time system, which can analyze data in real-time or near real-time as it is recorded.

In either type, the ECG signals are typically received from a plurality of leads that are attached between electrodes running between various points on the patient's body and/or an associated unit worn about the patient's neck, waist, wrist, and/or the like. Unfortunately, however, most, if not all, of the common portable, non-ambulatory devices are bulky and interfere with patients' normal lives. As a result, patient compliance cannot be relied upon to ensure proper use of ECG recording devices.

Other problems with body-worn, lead-type monitors include their inability to avoid attendant skin irritation. Results from such monitors can also vary depending on where various electrodes are placed on the patient's body. In addition, most leads need to be removed before showering, bathing, and/or other water exposure, as well as other activities.

Recently, portable, non-ambulatory ECG recording devices have become available that can operate on tactile-sensing from fingers and/or thumbs and/or hands of a patient without requiring placing leads and/or electrodes all over the patient's body. Such devices are often designed to be retained by patients long term, particularly as continuous-use monitors and/or recorders capable of displaying real-time results and/or subsequently transferring collected data to remote locations for time-delayed analysis.

In any event, many currently portable designs, while offering advantages over the prior art, are expensive to produce and maintain, and they are not generally intended for large-scale use. Accordingly, it is appropriate to consider new ECG devices that are affordable, self-contained, portable, disposable, designed for limited-use and/or large-scale use, and/or returnable to a central location for analyzing collected ECG data.

One scenario that exemplifies this need for improved portable, non-ambulatory, tactile-sensing ECG recording devices relates to dispensing new pharmaceuticals. For example, as is well-known, new drugs are subject to a rigorous evaluation process, from compound discovery to final approval, which can require years of trials and millions of dollars. Typically, new drugs are evaluated with progressive screening throughout so-called Phase I, II, and III clinical trials. Even after Phase III approval of a drug is received, however, there often remains a follow-up desire and/or requirement to perform a so-called Phase IV trial, which is also known as post-market surveillance. These Phase IV trials can be prudent even if a drug shows few complications during its Phase II and III trails, particularly as the drugs are dispensed to increasingly larger numbers of patients. Accordingly, new techniques are desirable, particularly during Phase II-IV trials, to allow for more ECGs to be acquired for review, without the necessity and burden of returning to a physician's office and/or other medical facility.

One critical component of this drug follow-up includes recording ECG signals, primarily to look for the existence of drug-induced LQTS and/or the like. As previously alluded to, LQTS describes an abnormality of the heart's electrical system, predisposing certain affected persons to dangerous heart rhythms, e.g. Torsade de Pointes, which can lead to a sudden loss of consciousness and/or death. As known, however, ECG recording devices can be used to measure QT intervals and screen for LQTS.

In a common scenario, a patient will take a particular medication for a particular period of time and then return to his or her physician's office, clinic, and/or other healthcare facility and/or the like that has a large, stand-alone ECG recorder. Unfortunately, repeatedly returning to such a facility can be expensive, time consuming, and impractical, particularly when drug-monitored patient populations exceed tens and hundreds of thousands of participants.

Besides drug-induced LQTS, it is also prudent to monitor for congenital LQTS, which is a genetic and/or inherited condition that can lead to fatal arrhythmias. Unfortunately, many of these types of arrhythmias can occur in young children during physical exertion (e.g., while exercising, playing an aerobic sport, and/or the like), and they are often fatal. Accordingly, an improved portable ECG recording device would allow for inexpensive screening of students, athletes, and/or the like to look for heart problems at an early age, particularly in a manner which is generally unavailable today.

Additionally, hospitals are prone to infections. For example, patients with severe infections, such as Methycillin-Resistant Staphylococcus Aureus ("MRSA"), may require monitoring ECG signals. However, after an MRSA ECG recording session, the ECG recording device must often be disinfected before it can be used again. Often, this involves detailed cleaning using severe cleaning agents, which can damage, and eventually destroy, the ECG leads. Accordingly, it is also important to consider new ECG recording techniques that can minimize problems associated with controlling infections.

In accordance with the foregoing, it is desirable to provide an improved, easy-to-use, portable, non-ambulatory, tactile-sensing ECG recording device that can be produced inexpensively, in large quantities, and adapted for large-scale use outside a traditional ECG facility. Such devices may be customized for particular patients picking up particular prescriptions, as well as for aggregated and/or other generalized screening purposes. It is also desirable to provide ECG recording devices that can be returned to a central location for further review and analysis following ECG data collection activities.

SUMMARY

In one embodiment, an electrocardiogram ("ECG") recording device comprises a mailable base and electrode assembly engageable with the base to receive ECG signals during a self-administered ECG examination.

In another embodiment, the ECG recording device comprises the mailable base and means engageable with the base for receiving the ECG signals.

In yet another embodiment, an ECG recording method comprises providing the mailable base and electrode assembly.

In yet still another embodiment, the ECG recording method comprises providing the mailable base and means engageable with the base for receiving the ECG signals.

In a further embodiment, a single-use or limited-use ECG recording device comprises a disposable or reusable or recyclable base and the electrode assembly.

And in another further embodiment, an ECG method comprises providing the disposable or reusable or recyclable base and electrode assembly.

BRIEF DESCRIPTION OF SEVERAL VIEWS OF THE DRAWINGS

A clear conception of the advantages and features constituting inventive arrangements, and of various construction and operational aspects of typical mechanisms provided by such arrangements, are readily apparent by referring to the following illustrative, exemplary, representative, and non-limiting figures, which form an integral part of this specification, in which like numerals generally designate the same elements in the several views, and in which.

DETAILED DESCRIPTION OF VARIOUS PREFERRED EMBODIMENTS

Referring now to the figures, preferred embodiments of the inventive arrangements will be described in terms of cardiac monitoring equipment. However, the inventive arrangements are not limited in this regard. For example, while variously described embodiments may provide self-administering ECG examinations in patient-monitoring contexts, other contexts are also hereby contemplated, including various other consumer, industrial, radiological, and inspection systems, and/or the like.

Figure 1:
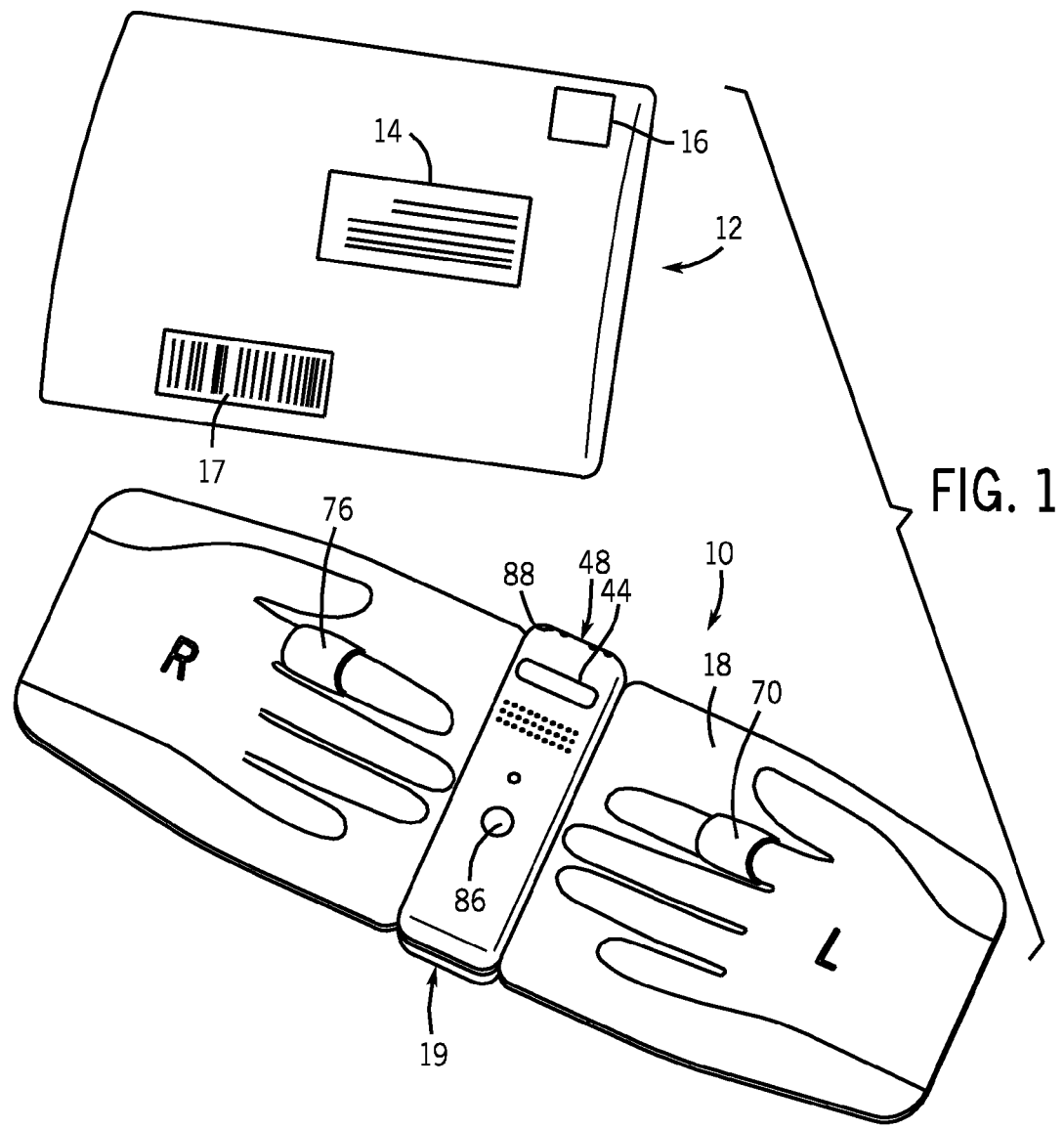
FIG. 1 is a perspective view of an ECG recording device and return mailer for returning the ECG recording device to a processing facility.

Referring now to FIG. 1, it depicts a portable, non-ambulatory, and non-invasive electrocardiogram ("ECG") recording device 10 that can be used to monitor and/or record ECG waveforms from a patient (not shown), preferably at a location remote from the patient's physician's office, clinic, and/or other traditional ECG-equipped facility. Preferably, the ECG recording device 10 is dispensed, such as at a pharmacy and/or other outlet, for example, along with a return mailer 12. In the embodiment shown in FIG. 1, the return mailer 12 preferably contains a mailing address 14 and/or prepaid postage 16. Preferably, the return mailer 12 also includes a bar code 17 and/or other similar tracking mechanism that can be used to identify the ECG recording device 10 when the ECG recording device 10 is returned to the mailing address 14 contained on the return mailer 12.

Figure 2:
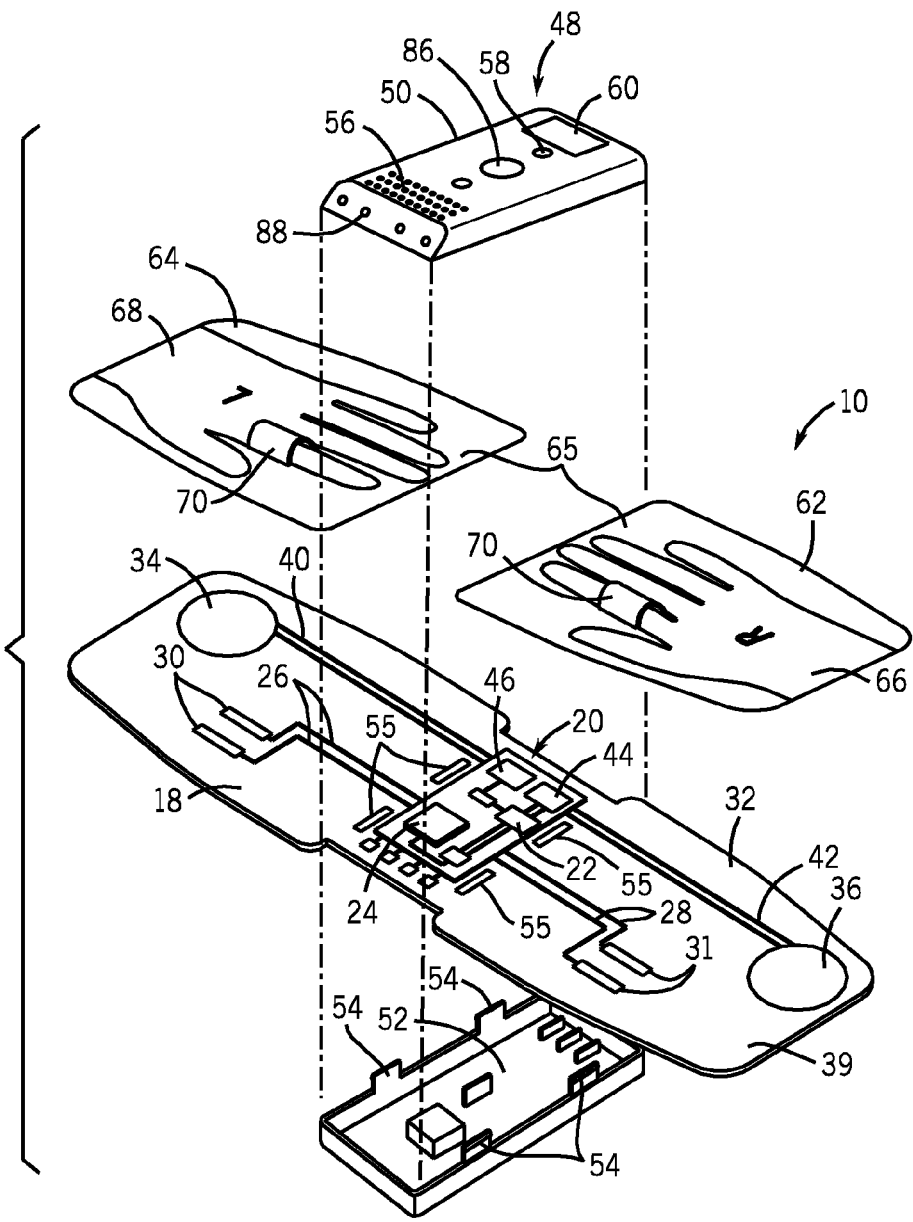
FIG. 2 is an exploded, perspective view of the ECG recording device of FIG. 1.

Now then, FIGS. 1-2 illustrate a first embodiment of the ECG recording device 10. In such an embodiment, the ECG recording device 10 includes a base 18, such as a flexible and/or semi-flexible base, such as formed from Mylar, extending on both sides of a control unit 19 centrally located thereabout.

Preferably, at least a portion of the base 18 is flexible enough so as to conform to various body shapes and/or sizes, particularly as it is held against a subject's abdomen, as will be elaborated upon.

Preferably, the control unit 19 includes an outer housing 48 that surrounds an internal control circuit 20. As shown in FIG. 2, the control circuit 20 preferably includes a power source 22, such as an ambient light receptor and/or battery, connected to a central processing unit ("CPU") 24 and/or the like. Preferably, the CPU 24 is in electrical communication with a pair of first leads 26 and a pair of second leads 28, each of which terminates at one or more respective contact pads 30, 31. Preferably, the contact pads 30, 31 are each mounted on a top surface 32 of the base 18.

Preferably, the base 18 further includes a first sensor pad 34 and a second sensor pad 36 formed on a bottom surface 39 of the base 18. Preferably, the first sensor pad 34 and second sensor pad 36 are electrically connected to the control circuit 20 by respective leads 40, 42. Preferably, the control circuit 20 further includes and/or is otherwise connected to a display 44 that allows the control circuit 20 to communicate messages to the patient. Preferably, the control circuit 20 further includes a push button 46 and/or the like that provides an input and/or output for the patient to communicate with the control circuit 20.

Preferably, the control circuit 20 is enclosed within the outer housing 48, which further includes a top section 50 and opposing bottom section 52. Preferably, both the top section 50 and bottom section 52 are formed from molded plastic and can include one or more interlocks 54 or the like that extend through one or more openings 55 formed in the base 18 to allow the top section 50 and the bottom section 52 to be secured to each other. Preferably, the top section 50 includes speaker openings 56, a push button opening 58, and/or a display window 60, preferably in mating alignment with the control circuit 20.

In a preferred embodiment, the ECG recording device 10 includes a first overlay 62 (e.g., right) and a second overlay 64 (e.g., left) that are each attachable to the base 18 to protect the control circuit 20 and leads 26, 28, 40, and 42, formed on the top surface 32 of the base 18. Preferably, both the first overlay 62 and second overlay 64 are adhered to the base 18 using conventional techniques, such as an adhesive.

Preferably, the first overlay 62 includes a graphic depiction 66 of a right hand of a patient while the second overlay 64 includes another graphic depiction 68 of a left hand of the patient. Preferably, these graphic depictions 66, 68 serve as guides for positioning the patient's hands on the ECG recording device 10.

Preferably, both the first overlay 62 and second overlay 64 each include an elastic finger cuff 70 that engages a portion of the index finger or other of the respective right and left hands of the patient while recording an ECG signal. Preferably, each finger cuff 70 includes a pair of electrodes that contact opposite sides of the patient's index fingers. Preferably, at least a portion of each finger cuff 70 is made from a suitable electrically conductive material.

In use, the pair of electrodes within the finger cuffs 70 contacts one of the contact pads 30, 31 formed on the base 18 when the first overlay 62 and second overlay 64 are adhered to the base 18. In this manner, electrical signals present on the skin of the patient can be detected and transferred to the CPU 24 through the first leads 26 and second leads 28.

Although the first overlay 62 and second overlay 64 are each shown including a finger cuff 70, it is further contemplated that the finger cuffs 70 could be replaced by tactile-sensing dry electrodes (not shown) formed on a top surface 65 of each of the overlays 62, 64. In such an embodiment, the electrodes could be contacted by the fingers of the patient's left and right hands during an ECG reading. Accordingly, the first leads 26 and second leads 28 would be coupled to such sensing electrodes and deliver sensed electrical signals to the CPU 24.

Figure 3:
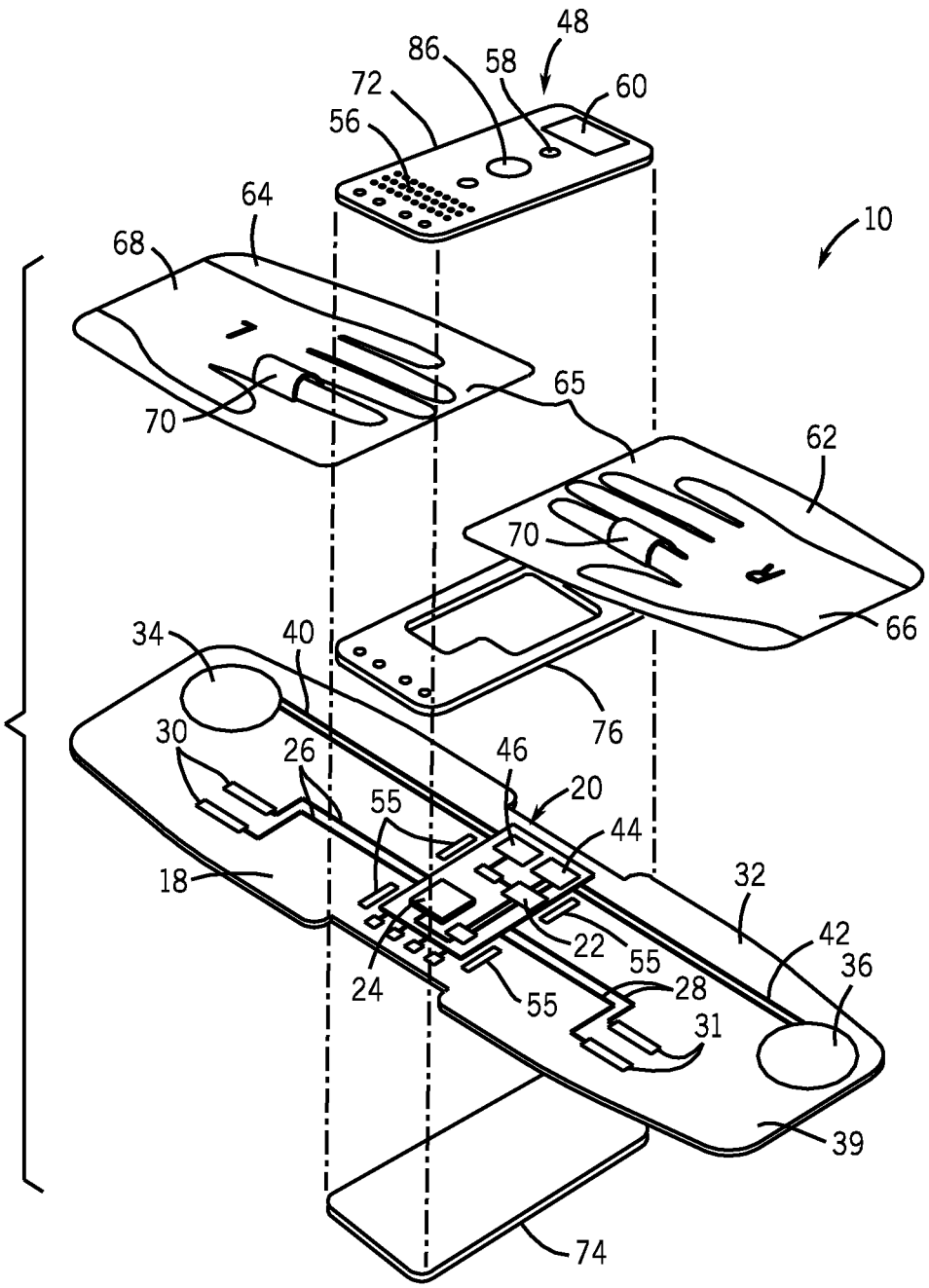
FIG. 3 is an exploded, perspective view of an alternative ECG recording device.

In addition to the first embodiment shown in FIGS. 1-2, FIG. 3 also illustrates a second embodiment of the ECG recording device 10. More specifically, in the embodiment shown in FIG. 3, the ECG recording device 10 uses eco-friendly packaging and components. For example, in the embodiment shown in FIG. 3, the base 18 can be formed from flexible, semi-flexible, foldable, rollable, and/or the like cotton fibers and cellulose paper, as compared to the Mylar base 18 previously described in FIGS. 1-2. In the embodiment shown in FIG. 3, the leads 26, 28, 40, and 42 can be printed on the base 18 with electrically-conductive soy ink and/or the like on the top surface 32 of the base 18. Preferably, at least one or both of the first sensor pad 34 and second sensor pad 36 can be likewise printed on the bottom surface 39 of the base 18, again using electrically-conductive soy ink and/or the like.

Preferably, the outer housing 48 in the second embodiment in FIG. 3 includes a cardboard top layer 72 and cardboard bottom layer 74 that protects the control circuit 20. Preferably, a cardboard spacer 76 can also be mounted to the top surface 32 of the base 18 to provide the required spacing for the control circuit 20.

In this second embodiment, the first overlay 62 and second overlay 64 are preferably formed from paper and include the finger cuffs 70, which can be formed from elastic materials with embedded electrode leads. Like the first embodiment, the electrode leads in each of the finger cuffs 70 contact one of the contact pads 30, 31 formed on the top surface 32 of the base 18 to relay the sensed signals to the control circuit 20. As can be readily understood from this description of FIG. 3, the second embodiment shown therein preferably forms most or all of its other layers from cellulose (e.g., paper and/or cardboard and/or other recyclable materials and/or the like), while the circuitry is connected using the electrically-conductive soy ink and/or the like. Thus, while re-cycling the eco-friendly ECG recording device 10 of FIG. 3, the soluble cellulose material can separate from the electronic parts, such that the entire ECG recording device 10, other than the control circuit 20, can be re-used and/or otherwise recycled.

Referring now back to FIG. 1, in use during an ECG reading, the electrodes in the pair of finger cuffs 70 contact the index fingers of the patient's left and right hands. Accordingly, the display 44 is preferably operated to provide a visually recognizable indication to the patient or others of the status of a particular ECG reading, such as when an ECG session is required, when to start and/or stop an ECG session, how long to conduct a particular ECG session, a number of times an ECG session can be initiated using the ECG recording device 10, and/or a quality measure of the strength or quality of a received ECG signal.

For example, during operation of the ECG recording device 10, the display 44 can be used to indicate that the signal quality is sufficient and/or that the ECG reading is proceeding accordingly. In alternate embodiments, the display 44 could also be a LCD display or series of e.g. red-yellow-green indicator lights to signify the status of the ECG session. In such embodiments, the display 44 could change during the ECG reading to indicate the status thereof.

In a contemplated embodiment of the inventive arrangements, after an ECG reading has been recorded, the CPU 24 could implement a counter (not shown) that can change after a successful ECG recording is taken and/or recorded using the ECG recording device 10. For example, in a count-down counter, the counter could count down to zero (or a like threshold), and upon reaching same, indicate to the patient that no more ECG readings are required or obtainable using that particular configuration of the ECG recording device 10. Once a counter has reached a specified threshold, the ECG recording device 10 can signal to the patient that the ECG recording device 10 should be returned to the healthcare facility and/or the like. Typically, once the desired number of readings have been made, the ECG recording device 10 is placed into the return mailer 12 of FIG. 1 and mailed or otherwise sent to a central location that can review and/or analyze the recordings taken by the ECG recording device 10. Alternatively, the ECG recording device 10 could also be returned to a pharmacy and/or other healthcare facility where it was received for such processing and/or other handling.

Figure 8:
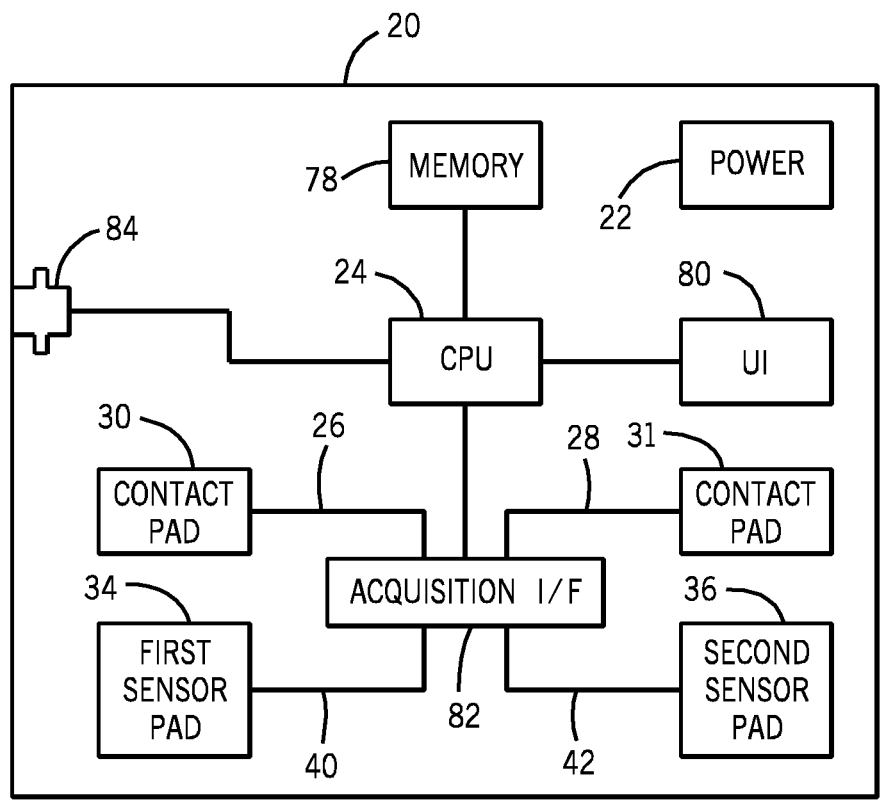
FIG. 8 is a high-level block diagram of a control circuit included as part of an ECG recording device.

Referring now to FIG. 8, it depicts a high-level block diagram of the control circuit 20, which preferably includes an internal or otherwise self-contained power source 22, such as an ambient light receptor and/or battery, which can power the internal components thereof (connections not shown). In the depicted embodiment, the CPU 24 interacts with a memory 78, which can be integrated with the base 18 or removable therefrom. In an embodiment wherein the memory 78 is removable from the base 18, it can be returned to the central location in addition to, or instead of, the entire ECG recording device 10 for processing the collected ECG data.

In any event, the CPU 24 also preferably interacts with a user interface 80, such as a tactile start button or other push button 46, as well as an acquisition interface 82. For example, the contact pads 30, 31, each of which is connected to one of the finger cuffs 70, are preferably in communication with the acquisition interface 82, which can convert analog information received through the respective leads 26, 28 into digital information that can be stored in the memory 78. In addition to receiving information from the contact pads 30, 31, the acquisition interface 82 can also receive analog information from the first sensor pad 34 and second sensor pad 36 through their respective leads 40, 42, which information can also be stored in the memory 78 after being converted into suitable digital form.

In the embodiment shown in FIG. 8, the control circuit 20 also includes an internal connector 84 that allows an external ECG processing system to be connected to the ECG recording device 10 once the ECG recording device 10 is returned to its specified location for analysis. In addition, the connector 84 can also be utilized to program a number of desired ECG readings to be made by the ECG recording device 10 prior to returning the same, or downloading additional information, such as demographics and/or tracking information and/or the like, about the patient, to the ECG recording device 10. Preferably, the connector 84 can implement technology such as "near field" or radio or infrared communications, such that it is not necessary to require actual physical connection to the ECG recording device 10. Instead, the collected ECG data can be transmitted to the ECG processing system wirelessly. For infection control concerns, for example, the ECG recording device 10 with collected ECG data can be sealed in a sterile plastic bag and then safely read by scanning the protected ECG recording device 10 using suitable wireless technology.

Referring back to FIG. 1, in a contemplated embodiment thereof, the ECG recording device 10 can also include a receptor, such a indentation 86, for a sealable blood well, along with a small pin (not shown) used to draw blood from the finger of the patient. Such a feature would allow for genetic testing, which can be useful in diagnosing arrhythmic abnormalities, for example. In addition, another input connector 88 can also be provided within the outer housing 48 to provide a further connection point to the control circuit 20, wherein, for example, a cable (not shown) with additional disposable leads (not shown) could be attached for obtaining additional information from the patient. These additional leads could allow, for example, screening of additional types of arrhythmic conditions, such as Brugada Syndrome, which requires leads V1, V2, and V3. Further, additional leads could also be utilized to detect acute myocardial infarction if, for example, a 12-lead reading was obtained. These additional leads could be standard ECG lead wires or a belt-style device that users could fit around the circumference of their chests to acquire the so-called "chest" leads of V1-V6, and/or other leads including those of a right side for a 15-lead ECG.

In other embodiments, the ECG recording device 10 can also be preprogrammed to beep or the like when it is time, for example, to take an ECG reading. This would require including e.g. an audio device (not shown), such as a piezoelectric speaker or buzzer, within the control unit 19, preferably operable in conjunction with the speaker openings 56.

The inventive arrangements further contemplate transmitting recorded ECG data back to a central receiving site without needing to mail back the ECG recording device 10. Accordingly, further optional considerations could include, for example, providing a speaker within the control unit 19 to allow for acoustically-driven transmissions. In this form, the user would dial a telephone number from a telephone and place the phone mouthpiece over the speaker so that recorded data can be modulated at a normal voice frequency and demodulated at the central receiving site. In another embodiment, it is envisioned to add a phone jack (not shown) to the control unit 19 so that when the ECG recording device 10 is plugged into the jack, it dials a preprogrammed telephone number and enables transmission back to the central site. Alternatively, a network connection could also be added to permit a network transfer of ECG data over a private or public network, such as the Internet, and then to the central site. Furthermore, data could also be optionally encrypted by the ECG recording device 10 and/or other for data transmissions and/or the like.

In one use of the ECG recording device 10, a patient picking up a prescription, such as from a pharmacy and/or the like, could be given the portable ECG recording device 10, which can be pre-programmed to request a predetermined set of ECG readings from the patient at prescribed intervals based upon the patient's drug therapy, for example. In this embodiment, the ECG recording device would be intended to be used by the patient at home and/or other locations remote from traditional points-of-care.

Figure 4:
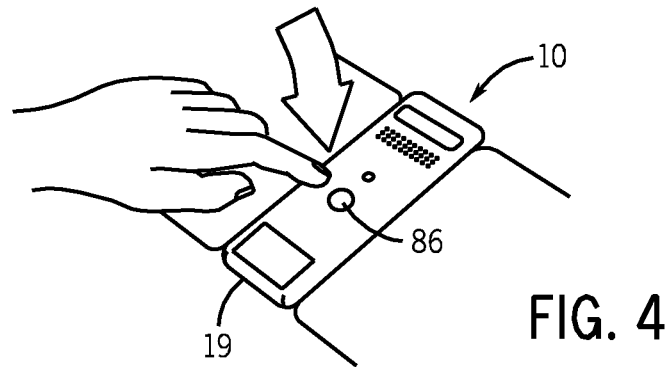
FIG. 4 is a view showing collection of a fluid sample by an ECG recording device.

When a patient is ready to take an ECG reading, in the embodiment of the ECG recording device 10 illustrated, the patient may first prick their finger with the pin included with the ECG recording device 10 and then deposit a blood sample within the indentation 86 shown in the figures, such as shown in FIG. 4. Once the blood sample has been placed in the indentation 86, the indentation 86 can then be sealed to create a blood well such that genetic testing and/or other types of blood testing can be carried out on the blood sample within the well at a subsequent time. Multiple and/or other bodily fluids can also be received.

Figure 5:
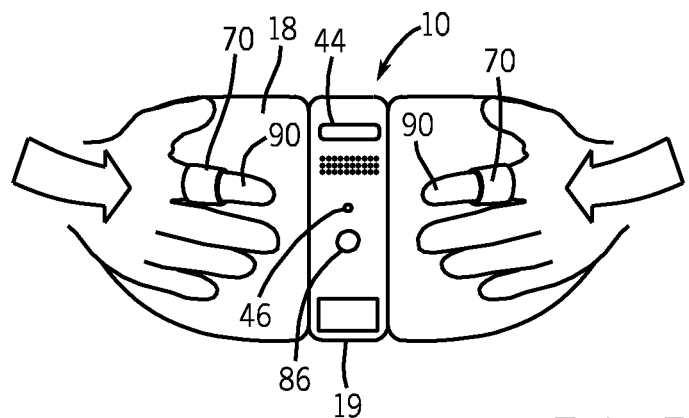
FIG. 5 is a view illustrating positioning a subject's hands within an ECG recording device.
Figure 6:
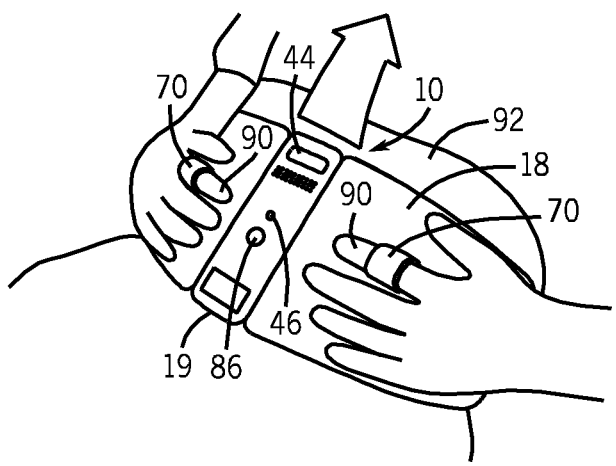
FIG. 6 is a view illustrating positioning an ECG recording device on a subject's abdomen.

After the blood sample has been taken and the patient is ready to take an ECG reading, the patient can position the bottom surface 39 of the base 18 on the bare skin of his or her abdomen 92 (e.g., see FIG. 6), such that each of the first sensor pad 34 and second sensor pad 36 are in direct contact with the skin of the subject's abdomen, and/or place the index fingers 90 of one or both of their right and left hands into the finger cuffs 70 (e.g., see FIGS. 5-6). As previously described, each of the finger cuffs 70 preferably includes a pair of electrodes that communicate with the control circuit 20 contained within the ECG recording device 10.

Figure 7:
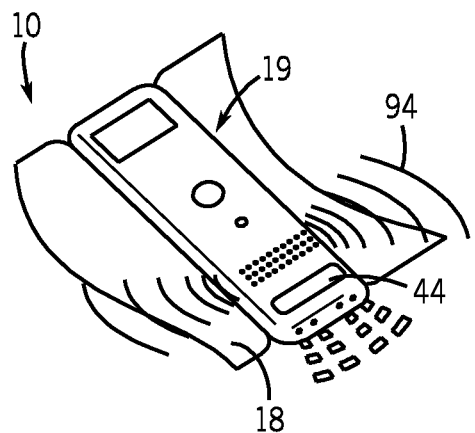
FIG. 7 is a view illustrating communication of control units of an ECG recording device.

Now then, if the patient has properly positioned the ECG recording device 10 on his or her abdomen 92 and/or properly inserted his or her index fingers into the finger cuffs 70, then the display 44 and/or the like can provide a status indication to the patient that the ECG recording device 10 is ready to operate and/or operating to record an ECG signal. Once the ECG recording device 10 has completed the ECG reading, then the display 44 can indicate that the reading is finished, prompting the patient to remove his or her hands from the finger cuffs 70 and/or remove the ECG recording device 10 from the patient's abdomen 92. As previously indicated, upon completing a successful ECG reading, a counter within the control circuit 20 can change until the counter reaches a pre-determined threshold, indicating no additional ECG readings are required. As illustrated in FIG. 7, for example, the ECG recording device 10 can communicate to the patient either through the display 44 or through audible signals 94 transmitted by a speaker contained within the control unit 19.

Once the ECG recording device 10 has recorded the desired number of ECG readings, then the patient is preferably prompted to return the ECG recording device 10, such as by U.S. mail and/or international mail and/or the like, using the return mailer 12, to a central location for further analysis and/or processing. If desired, the patient can be notified when the central location receives the patient's ECG recording device 10.

At the central facility, the ECG data stored in the control circuit 20 (e.g., the memory 78) can be read, analyzed, and/or otherwise processed, and the patient and/or patient's physician and/or the like can be advised of the ECG results. Once the ECG data has been read, the entire ECG recording device 10 can be disposed of and/or otherwise recycled. In the case of the embodiment shown in FIG. 3, for example, the entire ECG recording device 10, other than the control circuit 20, can also be reused and/or recycled.

Alternatively, or in addition to, the system that reads the ECG data and/or programs the ECG recording device 10 can also be programmed to call the patient on appropriate days to remind them to perform their ECG recording. In this embodiment, the patient may need to register at a secure website, for example. Registering at the website could also allow the patient to enter demographic and/or other health information about the patient, as well as any responses to other questions and/or provide other feedback.

While the ECG recording device 10 can be used with prescribed medication, it can also be provided in retail stores to allow individual consumers to acquire ECG data, which clinicians can then use to screen for cardiac problems. The ECG recording device 10, for example, can also be provided in schools and/or other community establishments and/or the like to enable ECG screenings, and it may also be useful in insurance evaluations and/or other applications as well.

Various embodiments of the inventive arrangements thus provide a portable, non-ambulatory, non-invasive, disposable ECG recording device 10, which can be customized and operated in a simple matter by a patient undergoing a prescribed drug therapy. The device can also be designed to be produced in quantities for large-scale use at low cost and/or intended to convey time-delayed data retrospectively, and various components thereof can be branded and/or left anonymous, as needed and/or desired. Preferably, the packaging of the ECG recording device 10 can be integrated for shipment thereof to the central location for analyzing the ECG recordings and/or reporting to the patient and/or a clinician and/or the like. In addition, the ECG recording device 10 can also be used in high-risk infection environments, without, for example, needing to clean and disinfect the same after every use.

Accordingly, it should be readily apparent that this specification describes illustrative, exemplary, representative, and non-limiting embodiments of the inventive arrangements. Accordingly, the scope of the inventive arrangements are not limited to any of these embodiments. Rather, various details and features of the embodiments were disclosed as required. Thus, many changes and modifications—as readily apparent to those skilled in these arts—are within the scope of the inventive arrangements without departing from the spirit hereof, and the inventive arrangements are inclusive thereof. Accordingly, to apprise the public of the scope and spirit of the inventive arrangements, the following claims are made:

What is claimed is:

1. A device for recording an electrocardiogram ("ECG") said device comprising:
   a base comprising a sheet of a flexible material with leads formed therein, the sheet having a first side and a second side, which are configured to conform to an abdomen of a subject, and a central portion formed between and integrally connected with the first side and the second side, the central portion having an area that is less than the area of either the first side or the second side;
   a first sensor pad and a second sensor pad formed on a bottom surface of respectively, the first side and the second side of the sheet, wherein the first sensor pad and second sensor pad are configured to receive an ECG signal from the abdomen of the subject;
   a control circuit disposed on a top surface of the sheet and centrally-located in the central portion between the first side and the second side, the control circuit coupled to the leads;
   an outer housing surrounding the control circuit, the outer housing comprising a top section that resides on the top surface of the sheet and a bottom section that resides on the bottom surface of the sheet, wherein both the top section and the bottom section comprise interlocks that penetrate through openings in the sheet proximate the central portion to secure the top section and the bottom section together to enclose the control circuit therein;
   an overlay engageable with the over the leads and forming a contact area that is sized and configured to receive a hand of a patient disposed flatly thereon; and
   a finger cuff disposed on the overlay, the finger cuff forming a loop configured to engage only one finger,
   wherein the control circuit is configured to receive via the leads at least one or more ECG signals from the finger cuff, the first sensor pad, and the second sensor pad during at least one or more self-administered ECG examinations.

2. The device of claim 1, wherein said device is configured to be self-contained.

3. The device of claim 2, wherein said device is configured to be battery-operated.

4. The device of claim 1, wherein said device is configured to be portable.

5. The device of claim 1, wherein said device is configured to be disposable.

6. The device of claim 1, wherein said device is configured to be mailable to a location remote from at least one of said ECG examinations.

7. The device of claim 1, wherein said device is configured to provide feedback to said subject.

8. The device of claim 7, wherein said device is configured to provide said feedback through a display.

9. The device of claim 8, wherein said device is configured in operative communication with said display.

10. The device of claim 8, wherein said display is integrated with said device.

11. The device of claim 1, wherein said device is configured to indicate its method of use.

12. The device of claim 11, wherein said device graphically depicts said method of use.

13. The device of claim 1, wherein at least a portion of the electrode assembly is made of an electrically conductive material and is printed on the sheet.

14. The device of claim 1, wherein at least a portion of said sheet is configured to conform to various abdomen shapes or sizes.

15. The device of claim 1, wherein said base contains a receptor for a liquid.

16. The device of claim 1, further comprising a memory configured to store said ECG signals.

17. The device of claim 16, wherein the memory is disposed on said base.

18. The device of claim 16, wherein the memory is removable.

19. The deice of claim 1, wherein the contact pads are disposed on opposite sides of the sheet.

20. The device of claim 1, further comprising a battery coupled to the control circuit.

21. The device of claim 1, wherein the first sensor pad and the second sensor pad are exposed on a bottom surface of the sheet.

22. The device of claim 1, wherein the overlay is constructed of a flexible material.

23. The device of claim 1, further comprising a display coupled to the control circuit, wherein the display is configured to provide a visually recognizable indication to the patient of the status of an ECG reading.

24. The device of claim 23, wherein said display is integrated with the control circuit.

25. The device of claim 24, wherein the display comprises a series of indicator lights which is configured to indicate the status of the ECG reading.

26. The device of claim 23, wherein the display comprises a LCD display which is configured to indicate the status of the ECG reading.

27. The device of claim 1, wherein the finger cuff is configured to engage a portion of each hand of the subject.

28. The device of claim 1, wherein the finger cuff includes a right-hand cuff and a left-hand cuff .

29. The device of claim 1, further comprising a sealable blood well.

30. The device of claim 1, further comprising a memory integrated with the control circuit.

31. The device of claim 30, wherein the memory is removable.

32. The device of claim 1, further comprising a connector coupled to the control circuit and which is configured to communicate the ECG signals from said control circuit to an ECG processing system.

33. A device for recording an electrocardiogram ("ECG"), said device comprising:
   a base comprising a sheet of a flexible material with leads formed therein, the sheet having a first side and a second side which are confined to conform to an abdomen of a subject and form a contact area that is sized and configured to receive a hand of a patient disposed flatly thereon, and a central portion formed between and integrally connected with the first side and the second side, the central portion having an area that is less than the contact area of either the first side or the second side;
   a control circuit disposed on the sheet coupled to the leads;
   an outer housing, surrounding the control circuit, the outer housing comprising a top section that resides on the top surface of the sheet and a bottom section that resides on the bottom surface of the sheet, wherein both the top section and the bottom section comprise interlocks that penetrate through openings in the sheet to secure the top section and the bottom section together;
   an overlay engageable with the sheet over the leads, the overlay comprising a graphic depiction of the hand of the subject to serve as a positioning guide, the overlay further comprising at least one finger cuff forming a loop coupled to the leads for engaging only one finger of at least one hand of the subject; and
   an electrode assembly coupled to the leads, wherein the electrode assembly is configured to receive at least one or more ECG signals from the finger and the abdomen of the subject,
   wherein the control circuit is configured to receive via the leads the ECG signals from the subject during at least one or more self-administered ECG examinations.

* * * * *

UNITED STATES PATENT AND TRADEMARK OFFICE
CERTIFICATE OF CORRECTION

PATENT NO. : 8,594,771 B2
APPLICATION NO. : 11/610995
DATED : November 26, 2013
INVENTOR(S) : Kohls et al.

It is certified that error appears in the above-identified patent and that said Letters Patent is hereby corrected as shown below:

In the Claims:

In Column 10, Line 11, in Claim 1, delete "("ECG")" and insert -- ("ECG"), --, therefor.

in Column 10, Line 21, in Claim 1, delete "surface of" and insert -- surface of, --, therefor.

In Column 11, Line 17, in Claim 19, delete "deice" and insert -- device --, therefor.

In Column 12, Line 13, in Claim 33, delete "side which are confined" and
insert -- side, which are configured --, therefor.

In Column 12, Line 22, in Claim 33, delete "housing," and insert -- housing --, therefor.

Signed and Sealed this
Twenty-fifth Day of March, 2014

Michelle K. Lee
*Deputy Director of the United States Patent and Trademark Office*